(12) United States Patent
Riggins et al.

(10) Patent No.: US 7,115,265 B1
(45) Date of Patent: Oct. 3, 2006

(54) FOUR GENETIC TUMOR MARKERS SPECIFIC FOR HUMAN GLIOBLASTOMA

(75) Inventors: Gregory J. Riggins, Durham, NC (US); Anita Lal, Durham, NC (US); William T. Loging, Salem, CT (US)

(73) Assignee: Duke University, Durham, NC (US)

( * ) Notice: Subject to any disclaimer, the term of this patent is extended or adjusted under 35 U.S.C. 154(b) by 0 days.

(21) Appl. No.: 09/853,880

(22) Filed: May 14, 2001

(51) Int. Cl.
*A61K 39/395* (2006.01)
*A61K 39/44* (2006.01)

(52) U.S. Cl. .................... 424/178.1; 424/181.1
(58) Field of Classification Search ............ None
See application file for complete search history.

(56) References Cited

U.S. PATENT DOCUMENTS

| | | | |
|---|---|---|---|
| 5,352,447 A | * | 10/1994 | Johnson et al. |
| 5,403,574 A | | 4/1995 | Piwnica-Worms |
| 5,801,154 A | | 9/1998 | Baracchini et al. |
| 6,025,473 A | | 2/2000 | Deeley et al. |
| 6,063,621 A | | 5/2000 | Deeley et al. |
| 6,080,842 A | | 6/2000 | Hillman et al. |

OTHER PUBLICATIONS

Braun et al (Genes Dev Jun. 1989;3(6):793-802).*
Lazarus LH et al (J. Neurosci. Methods Mar. 1998;23(2):161-72).*
Reiter et al (Clin Cancer Res Feb. 1996;2(2):245-52).*
Maynard et al (Annu. Rev Biomed Eng 2000;2:339-76).*
Curti (Clinical Reviews in Oncology/Hematology 1993;14:29-39).*
Jain (Science 1996; 271:1079-1080).*
Sirotnak, F.M., et al, "Co-administration of Probenecid, an Inhibitor of a cMOAT/MRP-like Plasma Membrane ATPase, Greatly Enhanced the Efficacy of a New 10-Deazaaminopterin against Human Solid tumors *in Vivo*[1]", Clinical Cancer Research, vol. 6, 3705-3712, Sep. 2000.
Demolombe, Sophie, et al, "ATP-binding cassette proteins as targets for drug discovery", Trends in Pharmacy Science, vol. 17, pp. 273-275, Aug. 1996.
Scheffer, George L., et al, "Specific Detection of Multidrug Resistance Proteins MFP1, MRP2, MRP3, MRP5, And MDR3, P-Glycoprotein with a Panel of Monoclonal Antibodies[1]", Cancer Research 60, pp. 5269-5277, Sep. 15, 2000.
Moody, T.W., et. al, "Neuromedin B-Like Peptides in Rat Brain: Biochemical Characterization, Mechanism of Release and Localization in Synaptosomes", Peptides, vol. 7, pp. 815-820, Mar. 1986.
Lazarus, L.H., et al, "Assessment of Neuromedin B Polyclonal antibodies as molecular probes in neural tissue", Journal of Neuroscience Methods, 23 pp. 161-172 (1988).
Siegfried, J.M, et al, "Evidence for Autocrine Actions of Neuromedin B and Gastrin-releasing Peptide in Non-small Cell Lung Cancer", Pulmonary Pharmacology & Therapeutics, vol. 12, pp. 291-302, (1999).
Hamazaki, H., "Neuromedin B", Progress in Neurobiology 62 pp. 297-312, (2000).
Kiaris, H. et. al. Inhibition of growth of human malignant glioblastoma in nude mice by antagonists of bombesin/gastrin-releasing peptide, Oncogene 18, pp. 7168-7173, (1999).
Aksoy, S. et al "Human Nicotinamide N-Methyltransferase Gene: Molecular Cloning, Structural Characterization and Chromosomal Localization", Genomics 29, pp. 555-561 (1995).
Sano, Akira. et. al "Fluorometric Assay of Rat Tissue N-Methyltransferases with Nicotinamide and Four Isomeric Methylnicotinamides", Chem. Pharm. Bull. 40 (1) pp. 153-156 (1992).
Rini, Josephine, "Human liver nicotinamide N-methyltransferase: ion-pairing radiochemical assay, biochemical properties and individual variation", Clinica Chimica Acta, 186 pp. 359-374, (1989).
Greenfield, Julia, et. al. "The Sec61 complex is located in both the ER and the ER-Golgi intermediate compartment" Journal of Cell Science 112, 1477-1486 (1999).
Wiertz, Emmanuel, et. al. "Sec61-mediated transfer of a membrane protein from the endoplasmic reticulum to the proteasome for destruction", Nature, vol. 384, Dec. 5, 1996.
Weterman, Marian, et al.,"A Novel Gene Is Expressed In Low-Metastatic Human Melanoma Cell Lines And Xenografts" Int. J. Cancer 60, pp. 73-81 (1995).
Ashley, D. et al., "Bone Marrow-Generated Dendritic Cells Pulsed With Tumor Extracts Or Tumor RNA Induce Antitumor Immunity Against Central Nervous System Tumors", J. Exp. Med., vol. 186, No. 7, pp. 1177-1182 (1997).
Loging, W.T., et al., "Identifying Potential Tumor Markers And Antigens By Database Mining And Rapid Expression Screening", Genome Res., vol. 10, No. 9, Abstract (2000).

* cited by examiner

*Primary Examiner*—Christopher Yaen
(74) *Attorney, Agent, or Firm*—Banner & Witcoff, Ltd.

(57) ABSTRACT

ABCC3, GPNMB, NNMT, and SEC61γ are expressed at higher levels in glioblastoma than in normal brain tissue. These four genes and their expression products are useful for diagnosing and treating glioblastoma and for identifying potential anticancer drugs.

7 Claims, No Drawings

SEQUENCE LISTING

<160> NUMBER OF SEQ ID NOS: 17

<210> SEQ ID NO 1
<211> LENGTH: 17
<212> TYPE: DNA
<213> ORGANISM: Artificial Sequence
<220> FEATURE:
<223> OTHER INFORMATION: PCR primer

<400> SEQUENCE: 1
cgtcttcccc tccatcg                                                  17

<210> SEQ ID NO 2
<211> LENGTH: 18
<212> TYPE: DNA
<213> ORGANISM: Artificial Sequence
<220> FEATURE:
<223> OTHER INFORMATION: PCR primer

<400> SEQUENCE: 2
ctcgttaatg tcacgcac                                                 18

<210> SEQ ID NO 3
<211> LENGTH: 20
<212> TYPE: DNA
<213> ORGANISM: Artificial Sequence
<220> FEATURE:
<223> OTHER INFORMATION: PCR primer

<400> SEQUENCE: 3
ttactttaat ttagaaatag                                               20

<210> SEQ ID NO 4
<211> LENGTH: 20
<212> TYPE: DNA
<213> ORGANISM: Artificial Sequence
<220> FEATURE:
<223> OTHER INFORMATION: PCR primer

<400> SEQUENCE: 4
atcaggtaat gcagtttgtt                                               20

<210> SEQ ID NO 5
<211> LENGTH: 19
<212> TYPE: DNA
<213> ORGANISM: Artificial Sequence
<220> FEATURE:
<223> OTHER INFORMATION: PCR primer

<400> SEQUENCE: 5
ctgcctagac ggtgtgaag                                                19

<210> SEQ ID NO 6
<211> LENGTH: 20
<212> TYPE: DNA
<213> ORGANISM: Artificial Sequence
<220> FEATURE:
<223> OTHER INFORMATION: PCR primer

<400> SEQUENCE: 6
agtggctggc tctgagtcac                                               20

<210> SEQ ID NO 7
<211> LENGTH: 22

```
<212> TYPE: DNA
<213> ORGANISM: Artificial Sequence
<220> FEATURE:
<223> OTHER INFORMATION: PCR primer

<400> SEQUENCE: 7
catcgacctg gagactgaca ac                                              22

<210> SEQ ID NO 8
<211> LENGTH: 20
<212> TYPE: DNA
<213> ORGANISM: Artificial Sequence
<220> FEATURE:
<223> OTHER INFORMATION: PCR primer

<400> SEQUENCE: 8
ccattctgcg gacatatttg                                                 20

<210> SEQ ID NO 9
<211> LENGTH: 19
<212> TYPE: DNA
<213> ORGANISM: Artificial Sequence
<220> FEATURE:
<223> OTHER INFORMATION: PCR primer

<400> SEQUENCE: 9
agccagcaag atccgagtg                                                  19

<210> SEQ ID NO 10
<211> LENGTH: 20
<212> TYPE: DNA
<213> ORGANISM: Artificial Sequence
<220> FEATURE:
<223> OTHER INFORMATION: PCR primer

<400> SEQUENCE: 10
gcacaatcta agccacgctg                                                 20

<210> SEQ ID NO 11
<211> LENGTH: 20
<212> TYPE: DNA
<213> ORGANISM: Artificial Sequence
<220> FEATURE:
<223> OTHER INFORMATION: PCR primer

<400> SEQUENCE: 11
gcaggcctgg tttattgaaa                                                 20

<210> SEQ ID NO 12
<211> LENGTH: 20
<212> TYPE: DNA
<213> ORGANISM: Artificial Sequence
<220> FEATURE:
<223> OTHER INFORMATION: PCR primer

<400> SEQUENCE: 12
ggttgcttca tccacacctt                                                 20

<210> SEQ ID NO 13
<211> LENGTH: 19
<212> TYPE: DNA
<213> ORGANISM: Artificial Sequence
<220> FEATURE:
<223> OTHER INFORMATION: PCR primer

<400> SEQUENCE: 13
```

```
aggtcacagg tctcgaaaa                                                     19
```

<210> SEQ ID NO 14
<211> LENGTH: 20
<212> TYPE: DNA
<213> ORGANISM: Artificial Sequence
<220> FEATURE:
<223> OTHER INFORMATION: PCR primer

<400> SEQUENCE: 14

```
agaggtggtg gaagaaactg                                                    20
```

<210> SEQ ID NO 15
<211> LENGTH: 20
<212> TYPE: DNA
<213> ORGANISM: Artificial Sequence
<220> FEATURE:
<223> OTHER INFORMATION: PCR primer

<400> SEQUENCE: 15

```
aactctaccc agtgtggaag                                                    20
```

<210> SEQ ID NO 16
<211> LENGTH: 20
<212> TYPE: DNA
<213> ORGANISM: Artificial Sequence
<220> FEATURE:
<223> OTHER INFORMATION: PCR primer

<400> SEQUENCE: 16

```
ttgaggaagt ggctaggatc                                                    20
```

<210> SEQ ID NO 17
<211> LENGTH: 560
<212> TYPE: PRT
<213> ORGANISM: Homo sapiens

<400> SEQUENCE: 17

```
Met Glu Cys Leu Tyr Tyr Phe Leu Gly Phe Leu Leu Leu Ala Ala Arg
  1               5                  10                  15

Leu Pro Leu Asp Ala Ala Lys Arg Phe His Asp Val Leu Gly Asn Glu
                 20                  25                  30

Arg Pro Ser Ala Tyr Met Arg Glu His Asn Gln Leu Asn Gly Trp Ser
             35                  40                  45

Ser Asp Glu Asn Asp Trp Asn Glu Lys Leu Tyr Pro Val Trp Lys Arg
 50                  55                  60

Gly Asp Met Arg Trp Lys Asn Ser Trp Lys Gly Arg Val Gln Ala
 65                  70                  75                  80

Val Leu Thr Ser Asp Ser Pro Ala Leu Val Gly Ser Asn Ile Thr Phe
                 85                  90                  95

Ala Val Asn Leu Ile Phe Pro Arg Cys Gln Lys Glu Asp Ala Asn Gly
                100                 105                 110

Asn Ile Val Tyr Glu Lys Asn Cys Arg Asn Glu Ala Gly Leu Ser Ala
            115                 120                 125

Asp Pro Tyr Val Tyr Asn Trp Thr Ala Trp Ser Glu Asp Ser Asp Gly
        130                 135                 140

Glu Asn Gly Thr Gly Gln Ser His His Asn Val Phe Pro Asp Gly Lys
145                 150                 155                 160

Pro Phe Pro His His Pro Gly Trp Arg Arg Trp Asn Phe Ile Tyr Val
                165                 170                 175
```

-continued

```
Phe His Thr Leu Gly Gln Tyr Phe Gln Lys Leu Gly Arg Cys Ser Val
            180                 185                 190
Arg Val Ser Val Asn Thr Ala Asn Val Thr Leu Gly Pro Gln Leu Met
            195                 200                 205
Glu Val Thr Val Tyr Arg Arg His Gly Arg Ala Tyr Val Pro Ile Ala
            210                 215                 220
Gln Val Lys Asp Val Tyr Val Thr Asp Gln Ile Pro Val Phe Val
225                 230                 235                 240
Thr Met Phe Gln Lys Asn Asp Arg Asn Ser Ser Asp Glu Thr Phe Leu
            245                 250                 255
Lys Asp Leu Pro Ile Met Phe Asp Val Leu Ile His Asp Pro Ser His
            260                 265                 270
Phe Leu Asn Tyr Ser Thr Ile Asn Tyr Lys Trp Ser Phe Gly Asp Asn
            275                 280                 285
Thr Gly Leu Phe Val Ser Thr Asn His Thr Val Asn His Thr Tyr Val
            290                 295                 300
Leu Asn Gly Thr Phe Ser Leu Asn Leu Thr Val Lys Ala Ala Ala Pro
305                 310                 315                 320
Gly Pro Cys Pro Pro Pro Pro Pro Pro Arg Pro Ser Lys Pro Thr
            325                 330                 335
Pro Ser Leu Gly Pro Ala Gly Asp Asn Pro Leu Glu Leu Ser Arg Ile
            340                 345                 350
Pro Asp Glu Asn Cys Gln Ile Asn Arg Tyr Gly His Phe Gln Ala Thr
            355                 360                 365
Ile Thr Ile Val Glu Gly Ile Leu Glu Val Asn Ile Ile Gln Met Thr
            370                 375                 380
Asp Val Leu Met Pro Val Pro Trp Pro Glu Ser Ser Leu Ile Asp Phe
385                 390                 395                 400
Val Val Thr Cys Gln Gly Ser Ile Pro Thr Glu Val Cys Thr Ile Ile
            405                 410                 415
Ser Asp Pro Thr Cys Glu Ile Thr Gln Asn Thr Val Cys Ser Pro Val
            420                 425                 430
Asp Val Asp Glu Met Cys Leu Leu Thr Val Arg Arg Thr Phe Asn Gly
            435                 440                 445
Ser Gly Thr Tyr Cys Val Asn Leu Thr Leu Gly Asp Asp Thr Ser Leu
            450                 455                 460
Ala Leu Thr Ser Thr Leu Ile Ser Val Pro Asp Arg Asp Pro Ala Ser
465                 470                 475                 480
Pro Leu Arg Met Ala Asn Ser Ala Leu Ile Ser Val Gly Cys Leu Ala
            485                 490                 495
Ile Phe Val Thr Val Ile Ser Leu Leu Val Tyr Lys Lys His Lys Glu
            500                 505                 510
Tyr Asn Pro Ile Glu Asn Ser Pro Gly Asn Val Val Arg Ser Lys Gly
            515                 520                 525
Leu Ser Val Phe Leu Asn Arg Ala Lys Ala Val Phe Phe Pro Gly Asn
530                 535                 540
Gln Glu Lys Asp Pro Leu Leu Lys Asn Gln Glu Phe Lys Gly Val Ser
545                 550                 555                 560
```

FOUR GENETIC TUMOR MARKERS SPECIFIC FOR HUMAN GLIOBLASTOMA

The U.S. Government has certain rights in this invention as provided for by the terms of Grant No. 98X-S146A awarded by the National Institutes of Health.

BACKGROUND OF THE INVENTION

During malignant progression, the pattern of expressed genes can provide clues to understanding tumor growth. In addition to insight into the tumor biology that might be derived from this pattern, there is a practical application for identifying genes highly expressed in tumors but not in normal adult tissue. A common example of tumor marker use is the serum protein assay for early detection of cancer (Kardamakis 1996). Investigators are also searching for genomic DNA alterations or abnormal gene expression in other clinically accessible samples. Progress has been made on finding tumor markers in stool (Sidransky et al. 1992; Vogelstein and Kinzler 1999), sputum (Mao et al. 1994), and urine (Lokeshwar et al. 1997).

Tumor-specific gene expression may also provide an opportunity for immune-based cancer therapies by targeting one or more of the tumor antigens coded for by these genes. Toxic antibodies with high affinity to accessible cell-surface or extracellular proteins may kill enough cancer cells to be therapeutic (Panchal 1998). Recent success with monoclonal antibody targeting of the Her/neu-2 receptor (Herceptin) indicates that targeting a tumor antigen can be useful (Hanna et al. 1999). The approach ideally requires identifying a cell surface protein uniquely expressed on the cells of the tumor, but not expressed in the patient's normal tissue exposed to the antibody during therapy. Also promising is a 'tumor vaccine' approach where the goal is to direct immune defenses toward the tumor by educating host antigen presenting cells with tumor-derived material (Gilboa et al. 1998). Expression of the marker on the cell surface is not a requirement of this system, but successful systemic administration of a tumor vaccine might require a relative lack of marker expression in all normal tissue cells, especially within vital organs. Either of these therapeutic approaches could benefit from the discovery of new tumor specific markers.

Tumor markers and antigens have promising clinical utility, but previous techniques for locating these proteins has not yielded robust markers for most cancers (Wu 1999). Finding a candidate marker is frequently the by-product of other studies, but not the initial intent of the research. Furthermore, generating the expression profile for each suspect gene has often relied on time consuming techniques, such as Northern blotting, in situ hybridization, or immunohistochemistry. Fortunately, new genome-scale technology should accelerate tumor marker discovery. In particular, the ability to assay comprehensive gene expression has made significant advances (Gress et al. 1992; Schena et al. 1995; Velculescu et al. 1995; Lockhart et al. 1996; Kononen et al. 1998).

Large-scale gene expression assays, such as cDNA microarrays (Schena et al. 1995), oligonucleotide chips (Lockhart et al. 1996), cDNA library sequencing (Adams et al. 1993), and Serial Analysis of Gene Expression (SAGE, (Velculescu et al. 1995) can decipher complex expression patterns. Much of the resulting data is being deposited on publicly accessible Web sites (Table 1) or is commercially available. Potentially, this information is a valuable resource, but mining the best data and adapting the results for a particular application is challenging. Follow-up and confirmatory studies are time consuming, and this problem will grow with the growth of large-scale expression technologies. A rapid confirmation of differential expression is useful prior to studies of gene function, or before investigating an over-expressed gene as a candidate tumor marker or antigen.

Candidate genes can be identified by mining public databases as in (Lal et al. 1999). Fluorescent-PCR expression comparison (F-PEC) to assess candidate gene expression on a panel of tumor and normal samples. The F-PEC method is based on continuous fluorescent monitoring of PCR products (Wittwer et al. 1997; Morrison et al. 1998) from a cDNA template. F-PEC allows for a quick and low-cost assessment of the expression pattern of a gene, uses commercially available instrumentation, and can be automated. Several candidate tumor markers were identified for glioblastoma multiforme [(GBM) WHO Astrocytoma Grade IV], which is the most common primary brain malignancy in adults, but which can occur at virtually any age (Kleihues et al. 2000). These genetic targets specific for GBM are useful for developing immune-based therapies. Now that expression information is readily available for many cancerous tissues, this approach can be employed to help find markers in other major tumors.

There is a need in the art to diagnose and treat glioblastoma and to identify anticancer drugs.

SUMMARY OF THE INVENTION

It is an object of the present invention to provide a method of diagnosing glioblastoma.

It is an object of the invention to provide a method of delivering a reagent to a glioblastoma.

It is another object of the invention to provide a method of treating a human with a glioblastoma.

It is yet another object of the invention to provide methods for screening for anti-cancer drugs.

These and other objects of the invention are provided by one or more of the embodiments described below.

In one embodiment of the invention, a method to aid in diagnosing glioblastoma is provided. The expression product of at least one gene selected from the group consisting of ABCC3, GPNMB, NNMT, and SEC61γ is detected in a first brain tissue sample suspected of being neoplastic and compared with expression second brain tissue sample which is normal. The expression product may be protein or RNA. Increased expression of the at least one gene in the first tissue sample relative to the second tissue sample identifies the first tissue sample as likely to be neoplastic.

In another embodiment of the invention a method of specifically delivering a reagent to a glioblastoma is provided. Cells of the glioblastoma are contacted with an antibody which is conjugated to a reagent and is specific for an extracellular epitope of ABCC3 or GPNMB. Upon contact between the cell and the antibody the reagent is delivered to the cell.

In even another emobodiment of the invention a method of treating a human with a glioblastoma is provided. Isolated dendritic cells of the human are contacted with an isolated and purified polynucleotide sequence of at least one gene selected from the group consisting of ABCC3, GPNMB, NNMT and SEC61γ. The isolated dendritic cells are then administered to the human.

In yet another embodiment of the invention a method of identifying a test compound as a potential anti-cancer drug is provided. A test compound is contacted with a cell which expresses at least one gene selected from the group consisting of ABCC3, GPNMB, NNMT, and SEC61γ. An expression product of the at least one gene is monitored. An expression product may be protein or RNA. A test compound which decreases the expression of the at least one gene is identified as a potential anti-cancer drug.

These and other embodiments of the invention provide the art with new methods for diagnosing glioblastoma, delivering reagents to glioblastomas, treating a human with a glioblastoma, and identifying potential anti-cancer drugs.

BRIEF DESCRIPTION OF PREFERRED EMBODIMENTS

EMBODIMENT 1. Process for finding candidate tumor markers uses fluorescent-PCR expression comparison (F-PEC). Genes over-expressed in tumors are mined from gene expression databases. A normalized cDNA panel is used to rapidly compare expression levels in malignant and normal tissues. The process requires an initial PCR to determine specificity of the primers, the product melting temperature and expression range of the tested samples. The highest expressing sample from the first PCR is serially diluted to create a standard curve for a second PCR, yielding information on the relative expression over several orders of magnitude.

EMBODIMENT 2 (A–D). Fluorescent-PCR verified a candidate glioblastoma marker, GPNMB.

EMBODIMENT 2A. Template cDNA from a bulk glioblastoma (GBM 861) and matched glioma/normal tissue pairs (GS 1099/Cortex1099 and AA1100/Cortex1100) were amplified with primers specific for GPNMB.

EMBODIMENT 2B. Melting curve analysis is performed simultaneously to optimize detection temperature, revealing a single peak consistent with a single amplification product.

EMBODIMENT 2C. After fluorescent-PCR, all reaction products were visualized on an agarose gel to verify a single product of the correct size.

EMBODIMENT 2D. Northern blot of normal fetal brain and three established GBM cell lines also show a difference in expression for GPNMB.

EMBODIMENT 3. Relative expression of the tumor markers was determined in 12 high-grade astrocytomas, one glioblastoma cell line (D450-MG), and normal tissues. Glioblastoma (GBM), gliosarcoma (GS), anaplastic astrocytoma (AA) and cortex samples from the same patient number indicated matched normal/tumor pairs removed during the same surgery. Gene expression levels determined by fluorescent-PCR were plotted relative to the highest expression tumor in each case. Gene expression was graphically displayed relative to serial dilutions of the highest expressing tumor.

EMBODIMENT 4 (A–B). Western Blotting of Annexin A1 was performed to compare protein levels from brain tumors, glioblastoma cell lines and normal neural tissue.

EMBODIMENT 4A. Expression in both glioblastoma cell lines (D392-MG, D450-MG & D534-MG) and primary GBM indicate that protein is expressed in transformed, but not normal (Cortex 1127, Cortex 1162 & Cortex 1421) tissues.

EMBODIMENT 4B. Normal tissues from different normal brain regions did not express high levels of ANXA1 protein compared to a glioblastoma (GBM 1132) or an oligodendroglioma (Oligo 1330).

DETAILED DESCRIPTION OF THE INVENTION

It is a discovery of the present inventors that ABCC3, GPNMB, NNMT, and SEC61γ are particularly useful for diagnosing and treating glioblastoma and identifying potential anticancer drugs.

According to the invention, the expression one of ABCC3, GPNMB, NNMT, and SEC61γ can be used to aid in diagnosing glioblastoma. Expression of ABCC3, GPNMB, NNMT, or SEC61γ in a tissue sample suspected of being neoplastic is measured and compared to expression of the same gene in a second brain tissue sample which is normal. Increased expression of the at least one gene in the first tissue sample relative to the second tissue sample identifies the first tissue sample as likely to be neoplastic.

The expression of the gene in the first tissue sample relative to the second tissue sample is preferably at least 2 fold, five fold, or most preferably, 10 fold higher. The expression product monitored may be RNA or protein. Methods of monitoring gene expression by monitoring RNA or protein levels are known in the art. RNA levels can be measured by any methods known to those of skill in the art such as, for example, differential screening, subtractive hybridization, differential display, and microarrays. A variety of protocols for detecting and measuring the expression of proteins, using either polyclonal or monoclonal antibodies specific for the proteins, are known in the art. Examples include Western blotting, enzyme-linked immunosorbent assay (ELISA), radioimmunoassay (RIA), and fluorescence activated cell sorting (FACS).

The first and second tissue samples may be from any mammal such as, for example, a mouse, a rabbit, a guinea pig, a dog, a cat, goat, a donkey, a cow, a horse, or most preferably from a human. Preferably, the first and second tissue samples are from the same mammal, most preferably the first and second tissue samples are from the same human.

According to the invention a reagent may be delivered to a glioblastoma using an antibody which specifically binds to an extracellular epitope of ABCC3 or GPNMB.

Preferably the antibody is ABCC3-specific or GPNMB-specific. The antibody can be specific for any epitope of ABCC3 or GPNMB, most preferably, the antibody is specific for an extracellular epitope of ABCC3 or GPNMB present at higher levels on glioblastoma cells relative to normal cells. Production of antibodies specific to a protein domain is routine, and can be done in a variety of ways known in the art including screening a phage-display library with the peptide of interest.

The reagent may be a chemotherapeutic agent, a cytotoxin, a radioactive compound, or a non-radioactive label. A chemotherapeutic agent may be compound with known anti-tumor effects such as cytosine arbinoside, fluorouracil, methotrexate or aminopterin, an anthracycline, mitomycin C, vinca alkaloids, demecolcine, etoposide, mithramycin, or an antitumor alkylating agent such as chlorambucil or malphalan. A cytotoxin, may be isolated from plants, animals, or bacteria. Plant derived toxins such as, for example ricin, taxol, or trematol may be used. Animal derived toxins such as, for example, tetrodotoxin, cobra venom, rattlesnake venom, or bungarotoxin, may be used. Bacteria derived toxins such as, for example, pertussis toxin or diptheria toxin may be used. A radioactive compound comprises an isotope which emits radioactivity such as, for example, radium, cesium 137, radioactive gold grains, iridium, strontium, indium 111, or cobalt. A non-radioactive label is a detectable label, such as a fluorescent, enzymatic, or chemiluminescent label such as horseradish peroxidase, alkaline phosphatase, or luciferase.

The glioblastoma may be in a human or a non-human, such as, for example a mouse, a rabbit, a guinea pig, a dog, a cat, goat, a donkey, a cow, or a horse. The glioblastoma may be multidrug-sensitive or multidrug-resistant.

According to the invention a human with a glioblastoma may be treated using a dendritic-cell based therapy. The principle of this approach is to educate antigen-presenting cells, such as dendritic cells, to recognize tumor antigens. One method is to remove dendritic cells from the human by leukophoresis, and to stimulate the dendritic cells (DCs) with RNA or protein that contains the antigen (or message for the antigen) specific to the tumor. The human's own DCs are then reintroduced, migrate to the lymph node, and present antigen to cytotoxic lymphocytes (CTLs). The activated CTLs then produce a toxic response to the antigen bearing (tumor) cells. Custom vaccine approaches can be based on the gene(s) that are most highly expressed in the human's tumors. Each tumor can be tested for expression of ABCC3, GPNMB, NNMT, and SEC61γ, and DCs trained with the most highly expressed antigen(s) for immunization. The administration of isolated and trained DC to the human can be by any method known in the art. Such methods include, but are not limited to, intraperitoneal, subcutaneous, intravenous, intrasplenic, intra-bladder, and intracranial injection.

Potential anti-cancer drugs can be screened for the ability to preferentially inhibit or kill cells expressing genes overexpressed in glioblastomas relative to normal cells by monitoring their effect on the expression products of such genes. Preferably, the gene is selected from the group consisting of ABCC3, GPNMB, NNMT, and SEC61γ. Potential anti-cancer drugs which can be tested include agents which are known in the art to have a pharmacological activity or can be compounds whose pharmacological activity is unknown. Compounds which can be tested include substances which are naturally occurring or which are designed in the laboratory, including members of small molecule libraries, protein libraries, nucleic acid libraries, etc. Test substances can be isolated from microorganisms, animals, or plants, or be produced recombinantly or by chemical synthesis. They can be purified or in mixtures in extracts. Therapeutic agents with known anti-tumor effects, such as cytosine arbinoside, fluorouracil, methotrexate or aminopterin, an anthracycline, mitomycin C, vinca alkaloids, demecolcine, etoposide, mithramycin, or an antitumor alkylating agent such as chlorambucil or malphalan can be tested for their efficacy against glioblastoma cells.

Any type of mammalian cell that can be maintained in culture or in an animal and can be transfected can be used. These cells include, but are not limited to, primary cells, such as glial cells, astrocytes, fibroblasts, myoblasts, leukocytes, hepatocytes, and endothelial cells, as well as cell lines (e.g., NCI-BL2126, Hs 578Bst, HCC1954 BL, Hs 574.Sk, Hs888Lu, which are available from the American Type Culture Collection, 10801 University Boulevard, Manassas, Va. 20110-2209). Cells lines derived from brain, liver, lungs, kidney, spleen, lymph nodes, breast, colon, bladder, muscle, prostate, cervix, bone, or skin, can be used. Preferred cells include tumor cells, preferably human tumor, more preferably human glioblastoma cells. Appropriate cells are, for example, glioblastoma cells, present either in situ in a mammalian body or in vitro in a tissue culture preparation. Tumor cells can be isolated from patients and placed in tissue culture. Alternatively, established tumor cell lines, such as A172, T98G, B104-1-1, DBTRG-05MG, MO59K, MO59J, NG108-15, U-87 MG, U-118 MG, U-138 MG, PI 153/3, HT29, SW480, HCT116, DLD1, MCF-7, HL-60, HeLa cell S3, K562, MOLT-4, Burkitt's lymphoma Raji, A549, G361, M12, M24, M101, SK-MEL, U-87 MG, U-118 MG, CCF-STTG1, or SW1088 can be used.

The expression product monitored may be RNA or protein. Methods of monitoring gene expression by monitoring RNA or protein levels are known in the art. RNA levels can be measured by any methods known to those of skill in the art such as, for example, differential screening, subtractive hybridization, differential display, and microarrays. A variety of protocols for detecting and measuring the expression of proteins, using either polyclonal or monoclonal antibodies specific for the protein are known in the art. Examples include enzyme-linked immunosorbent assay (ELISA), radioimmunoassay (RIA), and fluorescence activated cell sorting (FACS).

Preferably expression of at least one, at least two, at least three, or four of the genes selected from the group consisting of ABCC3, GPNMB, NNMT, and SEC61γ is monitored. The decrease in expression is preferably at least 2 fold, 5, or most preferably 10 fold.

A more complete understanding of the present invention can be obtained by reference to the following specific examples. These examples are provided for purposes of illustration only and are not intended to limit the scope of the invention.

EXAMPLE 1

Materials and Methods

Data Mining

Differentially expressed transcript targets were chosen from SAGE data housed at the CGAP Web site (http://www.ncbi.nlm.nih.gov/SAGE/) as described by (Lal et al. 1999). Currently, the Cancer Genome Anatomy Project (CGAP) is the primary public source for gene expression and, in particular, for brain tumors and normal neural tissues (see Table 1). Serial Analysis of Gene Expression (SAGE) data (Velculescu et al. 1995) from CGAP (www.ncbi.nlm.nih.gov/SAGE) was initially chosen for mining over expressed sequence tags (EST)-based libraries because SAGE libraries are not normalized and there are significantly more transcript tags available for analysis. This predicts a greater sensitivity for detecting low abundance transcripts in normal tissues.

SAGE tags from four bulk tissue libraries (SAGE_Duke_GBM_1110, SAGE_pooled_GBM, SAGE_BB542, and SAGE_normal_pool) were downloaded and compared for fold induction and statistical significance using the SAGE 300 program (http://www.sagenet.org/). Significance was based on Monte-Carlo simulations from this program, with a cut-off at p-chance=0.001. The SAGE libraries were made from two normal brain white matter libraries compared with two GBM bulk tumor libraries, with further details regarding each tissue sample located at the SAGEmap Web site (Table 1).

Tissue cDNA Panel

To verify SAGE predictions of expression and test expression in a wider range of tissue, particularly the expression pattern in an independent set of tumors and normal tissue, RNA was extracted from 27 tissues including high-grade astrocytic tumors, normal neural tissues, and normal vital organ tissues. Normally discarded tumor tissue was snap frozen, and was stored at −135° C. immediately after surgery and diagnosis. Final pathologic diagnosis of primary bulk tissues used for F-PEC confirmed eleven GBM (Grade IV astrocytomas) and one Grade III anaplastic astrocytoma (AA 1100). One gliosarcoma (GS 1099) is from a class of GBM variants that accounts for ~2% of glioblastomas (Kleihues et al. 2000). The cell lines (D392-MG, D450-MG, D534-MG) used for F-PEC, Northern blotting and Western blotting were well-established (greater than 70 passages), originally from an independent set of confirmed GBMs. One gliosarcoma variant, D392-MG, was within this set. Tumor tissue for Western blotting was also confirmed through clinical pathology as WHO grade IV glioblastoma multiforme (GBM1132, GBM1162, GBM1421 & GBM1330), plus one WHO grade II well-differentiated oligodendroglioma.

To control for varying amounts of cDNA, products from cDNA synthesis reactions were normalized to β-actin levels and the total DNA content in these samples was determined using a fluorescent probe with preferential binding to double-stranded nucleic acid. Controls for genomic DNA contamination were all negative. For the 27 samples there was a threefold range of fluorescence indicating that total cDNA amounts varied despite β-actin normalization. Further inspection of β-actin transcript levels in 15 tumor and normal bulk tissues from the SAGEmap database (Lal et al. 1999) showed a 10-fold range of expression, with 377±276 (mean±SD) transcripts per cell. These results suggested a problem with normalizing to β-actin. SAGE results predicted a tighter control for the s28 ribosomal transcript levels compared with p-actin (Velculescu et al. 1999), but variation in our panel, measured by fluorescent-PCR, was not significantly improved over p-actin variation. Such results indicate that normalization to a single housekeeping gene is likely to produce a wide variation in the fractional representation of the target gene from tissues of dissimilar origin. When genes from these tissues are being compared, a better approach should be to normalize by total cDNA levels, with a separate confirmation of the cDNA integrity- by fluorescent-PCR or other means-from a housekeeping gene.

RNA Isolation & cDNA Synthesis

Total RNA was isolated by separation on a cesium chloride gradient, and messenger RNA was purified from total using oligo-dT cellulose columns (New England Biolabs, Beverly, Mass.). Equal amounts of mRNA, as determined by RiboGreen fluorescence (Molecular Probes, Eugene, Oreg.), were used in identical cDNA synthesis reactions (Superscript II, Life Technologies, Gibco, Md.). The resulting cDNAs were screened for genomic contamination using genomic specific primers as well as confirming no amplification from control samples lacking reverse-transcriptase. All cDNA samples that lacked any detectable genomic DNA were then normalized to their cDNA concentrations as determined by PicoGreen (Molecular Probes, Eugene, Oreg.) binding fluorescence.

Northern Blotting

For Northern analysis, total RNA was isolated by CsCl ultracentrifugation. The normal RNA shown in FIG. 2D was fetal brain total RNA (Clontech, Palo Alto, Calif.). Hybridization probes were amplified from target gene sequences and β-actin. Equal amounts of total RNA, as determined by ultraviolet spectrophotometry, were separated on an agarose gel and blotted overnight before hybridizing them with a radioactively labeled PCR product.

Western Blotting

Though high levels of RNA transcripts can be predictive of high protein levels, protein levels must be confirmed if targeting the tumor antigen is the desired endpoint. For Western analysis, total cell lysates were prepared from corresponding cell pellets and frozen tissue samples. Normal tissue was also obtained from a non-cancer seizure patient (Cortex 1109, 1106, 1070) and rapid autopsy samples from normal individuals (cerebellum BB542 and Thalamus BB542). Equal amounts of protein from each sample were separated by electrophoresis and transferred to nitrocellulose membrane. Human Annexin A1-detecting antibody (Transduction Laboratories, Lexington Ky.) was incubated with the membrane for one hour, followed by subsequent incubation with horseradish peroxidase-conjugated sheep antimouse immunoglobulin. Protein was visualized by chemiluminescence (Amersham) and exposed to Kodak X-ray film from five to ten seconds. The molecular weights were determined by prestained standards (Life Technologies, Rockville Md.). Equivalent protein loadings were verified by staining the gel with Comassie blue after transfer.

Fluorescent-PCR Verification of Gene Expression

Fluorescent-PCR was performed using a thermocycler (LightCycler, Roche Diagnostics, Indianapolis, Ind.) with continuous monitoring of SYBR Green I (Molecular Probes, Eugene, Oreg.) fluorescence (Morrison et al. 1998) and normalized cDNA templates. The PCR reaction conditions were as follows: 67 mM Tris (pH 8.8), 16.6 mM $NH_4SO_4$, 6.7 mM $MgCl_2$, 10 mM β-mercaptoethanol, 0.5 μg/μl BSA, 1 μl of SYBR green diluted 1:1,500, 0.25 μM of each PCR primer, 200 μM of each dNTP, and 1 unit of platinum taq (Life Technologies) in a final volume of 20 μl.

Sample integrity was confirmed using primers specific for β-actin (5'-CGT CTT CCC CTC CAT CG [SEQ ID NO:1] AND 5'-CTC GTT AAT GTC ACG CAC [SEQ ID NO:2]). Optimal annealing conditions were determined for each set of gene-specific primers. Melting curve analysis was conducted for each set of gene-specific primers to refine PCR kinetics and conditions for each primer pair and to set the temperature for fluorescence reading between the melting temperature of any primer-dimer formation and the intended amplification product.

A 32 capillary sample rotor for the thermocycler was filled for each target assay, permitting an $H_2O$ control, positive control dilutions (to create a standard curve), an independent cell-line positive control, and 27 test samples. The expression levels for each transcript were assayed in twelve primary tumors, six normal brain samples, and nine other normal samples from vital organs. First-round assays were conducted to establish expression levels in normal and tumor tissue. Second-round reactions were conducted on each cDNA target using dilutions of the highest expressing tissue (determined from the first run) to compare relative expression of all samples without extrapolation beyond the standard curve. This additional run also served as a check of reproducibility.

Fluorescence curves obtained from the LightCycler™ system were analyzed by a second derivative fit for quantification analysis of transcript targets. The second derivative method used the point for which the rate of change of fluorescence is maximized, created a fit to the log-linear portion of the amplification curve, and extrapolated the starting concentration. Relative expression was determined by comparison to three control samples serially diluted 10-fold. After each assay, the reaction mixture was run on an agarose gel to visualize results and verify a single band of the correct size.

EXAMPLE 2

Identification of Candidate Genes with SAGE

SAGE tags—each representing one transcript—from surgically resected GBM and normal human brain white matter were downloaded, and their numbers were compared. The comparison reflected transcript levels of RNA derived from three normal samples compared to tumor-derived RNA from six patients. Candidate selection was based on consideration of relative fold induction in GBM compared with normal brain, lack of predicted expression in normal tissues, expression in the GBM cell line and, for some cases, a known membrane or extracellular localization of the protein. Electronic profiling of transcript numbers revealed 47,500 uniquely expressed neural genes of which 76 genes (0.16%) were over-expressed in the tumors to the order of 10-fold or more and with p values <0.001. Candidate tumor antigens were identified as those that exhibited significant expression of the gene in tumor combined with non-detectable expression in normal tissues, i.e., candidate tumor markers were identified by absolute differences in expression between tumor and normal tissues and not on small ratios of change. From the 76 candidates, 13 genes were chosen for further analysis. Genes that had little or no expression as detected by SAGE in normal brain and, preferably, coded for cell surface or excreted proteins were selected.

Regardless of the type or combination of data queried for genes over-expressed in tumors, there is still a need to confirm and expand the expression information. With a rapid confirmation process, candidates from multiple databases can be tested until the genes with the desired pattern of expression are elucidated.

It is possible that no single gene would be up regulated in all GBM, if these tumors arose through different molecular mechanisms. GBM are a heterogeneous group of tumors, with at least two distinct, molecular genetic pathways (Kleihues and Ohgaki 1999). The seven selected genes showed a significant increase in expression, on average, in only 3 of 12 of the tumors assayed. The composite expression showed that 8 of 12 glioblastomas had at least one marker that would discriminate between tumor and normal, with a difference in expression of at least 10-fold. The four remaining tumors with no marker expression may have similar histology, but the tumors were molecularly different, at least for these genes, from the original tumors used for the SAGE analysis that showed expression of these genes. Using the set of tumors with no candidate markers for further SAGE analysis, or selecting candidates from different databases, would perhaps yield markers specific to the remaining tumors. These or other tumor markers may provide a means to distinguish between different sub-classes of GBM.

Four of the seven potential glioblastoma tumor markers were previously implicated in cancer and had patterns of expression that would be consistent with overexpression in cancer. Neuromedin B, a bombesin-like growth peptide, is speculated to be an autocrine growth factor for lung cancer (Siegfried et al. 1999), but is likely expressed in normal anterior pituitary (Houben et al. 1993). SPARC, an extra-cellular matrix protein involved in tissue remodeling, is angiogenic (Jendraschak and Sage 1996) and is implicated in a number of different tumor types, including brain tumors (Ledda et al. 1997; Rempel et al. 1998; Rempel et al. 1999)]. ABCC3 is over-expressed in various cancer cell lines (Kool et al. 1999) and confers resistance to chemotherapy (Zeng et al. 1999). Annexin A1 is expressed in gastric cancers and breast carcinoma and is speculated to have immunosuppressive properties important for avoiding a host response to the tumor (Sakata et al. 1993; Ahn et al. 1997; Koseki et al. 1997). Annexin A1 has also been implicated in metastasis of breast adenocarcinomas (Pencil and Toth 1998).

If the tumor-specific expression pattern of identified genes is maintained at the protein level, the genes and their expression products can form the basis for anti-glioblastoma therapies. For example, an ATP-binding cassette, sub-family C Member 3 (ABCC3) protein, that has homology to multi-drug resistance-associated proteins (Kool et al. 1999) showed the highest induction over normal brain samples. ABCC3 is a transmembrane protein and is therefore a potential target for antibody therapy. However, expression of ABCC3 was observed in normal liver tissue, which would not make this gene a good target for systemic therapies, but perhaps useful for localized central nervous system targeting of GBM. For other targets, the possibility of insignificant expression in vital tissue remains, making these genes candidates for systemic therapy.

EXAMPLE 3

Annexin A1 Levels are Elevated in Cancerous Tissue

Western blotting was carried out as described above using commercial antibodies against Annexin 1 (Transduction Laboratories, Lexington Ky.). Strong reactivity was observed for GBM cell lines and most of the GBM bulk samples. Compared with a GBM positive control, normal cortex removed from an area adjacent to seizure foci, rapid autopsy cortex, cerebellum, and thalamus samples, all removed from patients without brain tumors, contained little or no detectable protein. One of four tissue samples initially diagnosed as normal cortex adjacent to a GBM was reactive for Annexin A1 (not shown) and may be contaminated with tumor cells since none of the six normal samples from non-cancer patients had detectable protein. The observation of elevated Annexin A1 protein levels in cancer is consistent with immunohistochemistry revealing reactivity in breast carcinomas, but not in normal breast tissue or most benign breast tumors (Ahn et al. 1997).

EXAMPLE 4

Fluorescent PCR Verification of SAGE Results

Real-time fluorescent PCR has the potential to measure gene expression rapidly in multiple samples and to do so with very sensitive levels of detection (Freeman et al. 1999), capabilities that made evaluating the expression pattern of the mined genes more efficient. PCR primer sets were selected for each candidate gene (Table 2) and optimized for use with the LightCycler™, one of several thermal-cycling machines available that is capable of continuous fluorescence monitoring. To make the F-PEC procedure rapid and inexpensive, we avoided the use of fluorescent-labeled hybridization primers. We first tested SYBR green, a fluorescent DNA binding dye with specificity for double-stranded DNA used previously for this purpose (Morrison et al. 1998). The combination of SYBR green, a 'hot-start' type taq polymerase and a modified PCR buffer worked robustly and was relatively inexpensive. To eliminate the potentially confounding effects of primer-dimer amplification, the fluorescence was measured at a temperature below the melting point of the products and above the melting point of the primer-dimers that formed in some reactions. The assay proved to be proportional to the starting cDNA concentrations as determined by serial dilution experiments. Assays using additional fluorescent primers that hybridizes within the PCR product (e.g., 'taq-man' or fluorescent resonant energy transfer primers) may provide additional assay specificity and sensitivity, but might prove difficult to optimize for a rapid screening procedure.

Eight samples were used to represent normal neural tissues for the F-PEC panel: four normal cortex samples that were adjacent to four of the above tumors and RNA purchased from two different adult whole brains, spinal cord, or cerebellum (Clontech, Palo Alto, Calif.). Histology from one margin of ~5 mm pieces of tissue obtained during tumor resection was used to identify the 'normal' brain samples derived from brain tumor patients. Non-neural tissues were also procured in the above fashion either commercially (heart, kidney, liver, and lung) or from autopsy tissue (tonsil, bone marrow, and trachea).

Of 13 genes tested for gene expression levels in our cDNA panel, we identified primer pairs for 11 that produced satisfactory PCR amplification for the fluorescent-PCR assay. Conditions were optimized to produce a single PCR product band at the predicted fragment length. Next, the entire normal and tumor tissue panel was assayed to determine the tumor with the highest level of expression. If the initial profile showed increased expression in tumor samples, then the highest expressing tumor was used as a serially diluted standard for a second PCR-based comparison of the sample panel. This second round served as a reproducibility check and ensured that the gene expression levels of all the tissues could be compared simultaneously without extrapolation beyond the standard curve. An outline of the overall approach is shown in FIG. 1, and examples of the results are shown in FIG. 2. The optimization of a gene-specific assay is rapid and requires the purchase of only one or two unmodified PCR primer pairs per gene. The scheme presented here provides a system that is straightforward to apply with the possibility for higher throughput automation.

EXAMPLE 5

Custom Designed Dendritic Cell or Tumor Vaccine Therapy

Dendritic cells are isolated as described in Ashley, et al. (1997) *J. Exp. Med.*, 186(7): 1177–82, which is incorporated herein by reference. Briefly, bone marrow is flushed from the long bones of C57BL/6 mice and depleted of red cells with ammonium chloride treatment. Bone marrow cells are then depleted of lymphocytes, granulocytes, and Ia+ cells using a mixture of monoclonal antibodies (2.43, 53–6.7) and complement. Cells were plated at $10^6$ cells/ml in 6 well plates in RPMI 1640 medium supplemented with 5% heat-inactivated FCS, 50 mM 2-mercaptoethanol, 10 mM Hepes (pH 7.4), 2 mM glutamine, 100 U/ml penicillin, 100 mg/ml streptomycin, and 3.3 ng/ml GM-CSF (Amgen). After three days of culture, floating cells were gently removed and fresh medium was added. After seven days of culture, non-adherent cells and loosely adherent proliferating dendritic cell aggregates were collected and replated in 10 mm Petri dishes at $10^6$ cells/ml. After 10 days of culture, nonadherent cells were removed for analysis and immunization.

Total RNA is isolated from actively growing tissue culture tumor cells. 25 µg/250 µl Opti-MEM (GIBCO BRL) RNA is mixed with 50 µg/250 µl Opti-MEM of the cationic lipid DOTAP (Boehringer Mannheim) in 12×75 m polystyrene tubes at room temperature for 20 minutes. The RNA-DOTAP mixture is added to $2-5\times10^6$ cells/ml dendritic cells in serum free Opti-MEM medium and incubated at 37° C. in a water bath with occasional agitation for 20 min. The dendritic cells are then washed twice and resuspended in PBS at $10^5/500$ µl for intraperitoneal immunization. $10^5$ cells/500 µl were injected into each mouse.

Cytotoxic T lymphocytes are isolated from spleens of immunized and control mice and restimulated in vitro for five days on irradiated tumor cells. Cytotoxic activity is tested by killing of $^{57}Cr$-pulsed tumor cells.

EXAMPLE 6

Custom Designed Antibody-Based Therapy

An extracellular epitope of a protein overexpressed on tumor cells relative to normal cells is identified. Antibodies are generated against the epitope by any means known in the art. The antibodies are conjugated to a chemotherapeutic reagent and administered to the patient, preferably intraperitoneally. Antibodies will target the tumor cells and deliver the chemotherapeutic reagent. This approach can form the basis of a locally based therapy, i.e., therapy within the CNS compartment. Such therapeutic approaches may have an advantage because they may still be useful even if there is gene expression in a distant normal tissue that does not come in contact with the therapy.

EXAMPLE 7

Refining Gene Expression Assays

A significant problem with any gene expression assay is assessing the purity of the samples tested. Primary tumor tissue has varying degrees of normal cells, and 'normal' tissue obtained during tumor resection may have occult malignant cells. For example, infiltration by macrophages into the tumor samples might produce a marker against a non-malignant cell population. To guard against this latter possibility, additional expression in well-established glioblastoma cell lines, presumed to be a purely malignant cell population, for both the candidate selection and F-PEC analysis can be measured. When high expression of these genes was observed in a GBM cell line, it suggested that expression in the bulk tumor was from transformed cells and not from normal cells.

Another potential problem with this approach is unrecognized gene expression in a small but vital normal cell population. Assaying a greater range of normal tissues or defined cell populations can perhaps minimize this. Certainly, the existence of a desirable expression pattern in a potential tumor marker is only suggestive of its potential as a truly useful marker. Further immunohistochemical or in situ hybridization of tissue sections will be required on a culled set of the most promising tumor marker candidates. Since development of novel antibodies is time consuming and expensive, the F-PEC approach may be useful in triaging candidates prior to antibody design and synthesis. Additionally, F-PEC could be readily applied to laser-captured microdissected cells to ensure a greater level of sample purity (Simone et al. 1998).

Of the 11 candidate genes assayed, 4 were deemed unacceptable due to either high level of expression in one of the neural-derived tissues (CSRP2, S100A4, and CXCR4) or was expressed in only one tumor from the panel (GCS1).

Seven genes showed a distinct difference in transcript levels between normal neural tissues and some GBMs (FIG. 3).

Though genes can be found using this procedure that have a promising pattern of RNA expression several errors are inherent with this approach. PCR-based assays may suffer from sequence variations at the primer sites, differential splicing, or spurious amplification from related cDNA sequences. This study detected one instance of inconsistency between the Northern blot result and the F-PEC results. There was not consistent PCR amplification in a cell line where a band was observed on a Northern blot, but not amplified by PCR. The 1.4 kb PCR product length may have been too long to amplify consistently. Concordant results between the two methods for all samples were achieved after spacing the PCR primers closer together. Based on this observation, amplification products should be designed to be smaller than ~300 bp for the F-PEC procedure.

There are other approaches for mining over-expressed genes. For example, a recently developed prediction algorithm for tumor marker discovery from EST data could also improve and supplement the initial candidate selection process (Walker et al. 1999). Many of the Web sites listed in Table 1 have included tools to mine data, and data from these sites can be combined to enhance selection.

Another approach to enhance tumor marker discovery is tissue microarray technology. Tissue microarrays can simultaneously probe expression in hundreds or thousands of tissue cores (Kononen et al. 1998; Moch et al. 1999). F-PEC data could augment tissue microarray analysis, in particular when an antibody or in situ hybridization assay in not readily available for a particular gene. Regardless of the follow-up approach, there is a real need to be able to rapidly assess well-documented samples for expression of genes initially identified by comprehensive gene expression technologies.

This study shows that tumor marker discovery can be enhanced by using public gene expression data followed by rapid expression screening to locate candidate tumor markers for GBM. This study does not search for all the possible database-mined candidate genes. However, it does indicate that there are some genes that are highly expressed in a portion of GBM but not in surrounding normal neural tissue. These data also suggest that there is no single highly expressed gene common to all tumors classified by histology as GBM. Still, the combination of genes identified by this approach may be useful for therapy or prognosis. Continued application of F-PEC to the increasing amount of large-scale expression data should yield additional tumor marker candidates. This approach can be easily adapted and applied to various tumor types, in particular to test candidate genes mined from public databases.

TABLE 1

Human gene expression databases

| Web site | URL | Tissues | Description |
|---|---|---|---|
| ArrayExpress Database | www.ebi.ac.uk/arrayexpress | pending | Planned public repository of microarray data. |
| Body Map | bodymap.ims.u-tokyo.ac.jp | Various normal & tumor | Based on EST sequencing of ~3,000 reads each from 60 tissues. |
| Brown Lab | cmgm.stanford.edu/pbrown | Cultured fibroblasts & B-cell lymphoma. | Custom cDNA array data and supplemental information. |
| CGAP cDNA xProfiler | www.ncbi.nlm.nih.gov/ncicgap/cgapxpsetup.cgi | Most normal and tumor tissues | Can search for cDNA library specific transcripts based on EST sequencing. Most extensive profile. |
| CGAP SAGEmap | www.ncbi.nlm.nih.gov/SAGE | Brain, colon, ovary, prostate & breast; tumor & normal | Ongoing SAGE expression analysis of cancer. ~50,000 tags from each of 68 tissues and cell lines. |
| Developmental Therapeutics | www.dtp.nci.nih.gov | NCI panel of 60 cancer cell lines | Microarray and drug response data for NCI60 cell lines. |
| Gene Expression Omnibus (GEO) | www.ncbi.nlm.nih.gov/geo | pending | Future public repository and comparison interface for all types of expression data. |
| Human Gene Expression Index (HuGE) | www.hugeindex.org | Normal blood, kidney, cervix & vulva | Affymetrix chip based database, expanding to cover many normal tissues. |
| Prostate Expression Database | chroma.mbt.washington.edu/PEDB | Prostate normal, pre-malignant and cancer | Expression based on 60,000 ESTs in an easily queried interface. |
| SAGEnet (Kinzler-Vogelstein Lab) | www.sagenet.org | Normal colon, colon & pancreas cancer | Over 400,000 SAGE transcript tags in downloadable files for local analysis. |
| Genexpress - CNRS | idefix.upr420.vjf.cnrs.fr/EXPR/ | Brain, muscle & other normals | 5,058 brain or muscle derived genes probed by filter array. |
| TIGR Human Gene Index | www.tigr.org/tdb/hgi/hgi.html | Most normal tissues | Has query interface for tissue specific ESTs. |
| Whitehead/MIT Genome Center's Molecular Pattern Recognition web site | waldo.wi.mit.edu/MPR | Leukemias & Hematopoeitic cell lines | Affymetrix based array data available for download. |

TABLE 2

Candidate glioblastoma tumor markers

| Gene name (synonym) | Symbol (GenBank#) | Cellular location | Primer pairs | $^{1}T_{a}$ ° C. |
|---|---|---|---|---|
| Sec61 gamma | SEC61G (AF054184) | ER-Golgi (Greenfield and High 1999) | TTA CTT TAA TTT AGA AAT AG/ ATC AGG TAA TGC AGT TTG TT (SEQ ID NO 3 and 4) | 50 |
| Nicotinamide N-methyltransferase | NNMT (U08021) | Cytoplasm (Aksoy et al. 1994) | CTG CCT AGA CGG TGT GAA G/ AGT GGC TGG CTC TGA GTC AC (SEQ ID NO: 5 and 6) | 55 |
| ATP-binding cassette, sub-family C Member 3 (MLP2, MRP3, CMOAT2) | ABCC3 (AB010887) | Membrane (Kiuchi et al. 1998) | CAT CGA CCT GGA GAC TGA CAA C/ CGA TTC TGC GGA CAT ATT TG (SEQ ID NO 7 and 8) | 58 |
| Neuromedin B (NMB) | NMB (M21551) | Secreted (Krane et al. 1988) | AGC CAG CAA GAT CCG AGT G/ GCA CAA TCT AAG CCA CGC TG (SEQ ID NO: 9 and 10) | 50 |
| Annexin A1 (lipocortin 1, LPC1) | ANXA1 (X05908) | Membrane (Wallner et al. 1986) | GCA GGC CTG GTT TAT TGA AA/ GGT TGC TTC ATC CAC ACC TT (SEQ ID NO: 11 and 12) | 53 |
| SPARC: secreted protein, acidic, cysteine-rich (osteonectin) | SPARC (J03040) | Secreted (Lane and Sage 1994) | AGG TCA CAG GTC TCG AAA A/ AGA GGT GGT GGA AGA AAC TG (SEQ ID NO: 13, and 14) | 53 |
| Glycoprotein (transmembrane) nmb | GPNMB (X76534) | Membrane (Weterman et al. 1995) | AAC TCT ACC CAG TGT GGA AG/ TTG AGG AAG TGG CTA GGA TC (SEQ ID NO 15 and 16) | 55 |

$^{1}T_{a}$ refers to the annealing temperature used for fluorescent-PCR amplification.

REFERENCES

1. Adams, M. D., et al. (1993) Nat. Genet. 4: 373–80.
2. Ahn, S. H., et al (1997) Clin Exp Metastasis 15: 151–6.
3. Aksoy, S., et al. (1994) J. Biol. Chem. 269: 14835–40.
4. Avigan, D. (1999) Blood Rev. 13: 51–64.
5. Bjorck, P. (1999) Clin. Immunol. 92: 119–27.
6. Freeman, W. M., et al. (1999) Biotechniques 26: 112–22, 124–5.
7. Gilboa, E., et al. (1998) Cancer Immunol. Immunother. 46: 82–7.
8. Greenfield, J. J. and S. High. (1999) J Cell Sci. 112: 1477–86.
9. Gress, T. M., et al. (1992) Mamm. Genome 3: 609–19.
10. Hanna, W., et al (1999) Mod Pathol 12: 827–34.
11. Houben, H., A et al. (1993) Mol. Cell. Endocrinol. 97: 159–64.
12. Jendraschak, E. and E. H. Sage. 1996. Semin. Cancer Biol. 7: 139–46.
13. Kardamakis, D. 1996. Anticancer Res. 16: 2285–8.
14. Kiuchi, Y., et al. (1998) FEBS Lett. 433:149–52.
15. Kleihues, P., et al. (2000) Pathology & Genetics: Tumours of the Nervous System (ed. P. Kleihues and W. K. Cavenee). International Agency for Research on Cancer, Lyon.
16. Kleihues, P. and H. Ohgaki. 1999. Neuro-Oncology 1: 44–51.
17. Kononen, J., et al. (1998) Nat. Med. 4: 844–7.
18. Kool, M., et al. (1999) Proc. Natl. Acad. Sci. USA 96: 6914–9.
19. Koseki, H., et al. (1997) Surg. Today 27: 30–9.
20. Krane, I. M., et al. (1988) J Biol Chem 263: 13317–23.
20. Lal, A., et al. (1999) Cancer Res. 59: 5403–7.
21. Lane, T. F. and E. H. Sage. (1994) Faseb J 8: 163–73.
22. Ledda, M. F., et al. (1997) Nat. Med. 3: 171–6.
23. Lockhart, D. J., et al. (1996) Nat. Biotechnol. 14: 1675–1680.
24. Lokeshwar, V. B., et al. (1997). Cancer Res. 57: 773–7.
25. Mao, L., et al. (1994) Proc. Natl. Acad. Sci. USA 91: 9871–5.
26. Moch, H., et al. (1999) Am. J. Pathol. 154: 981–6.
27. Morrison, T. B., et al. (1998) Biotechniques 24: 954–62.
28. Panchal, R. G. (1998) Biochem. Pharmacol. 55: 247–52.
29. Pencil, S. D. and M. Toth. (1998) Clin Exp Metastasis 16: 113–21.
30. Rempel, S., S. Ge, and G. JA. (1999) Clin. Cancer Res. 5: 237–41.
31. Rempel, S. A., et al. (1998) J. Neuropathol. Exp. Neurol. 57: 1112–21.
32. Sakata, T., et al. (1993) J. Immunol. 151: 4964–72.
33. Schena, M., et al. (1995) Science 270: 467–470.
34. Sidransky, D., et al. (1992) Science 256: 102–5.
35. Siegfried, J. M., et al. (1999) Pulm. Pharmacol. Ther. 12: 291–302.
36. Simone, N. L., R et al. (1998) Trends Genet 14: 272–6.
37. Strausberg, R. L., et al. (1997) Nat. Genet. 15: 415–6.
38. Velculescu, V. E., et al. (1999) Nat. Genet. 23: 387–388.
39. Velculescu, V. E., et al. (1995) Science 270: 484–487.
40. Vogelstein, B. and K. W. Kinzler. (1999) Proc. Natl. Acad. Sci. USA 96: 9236–41.
41. Walker, M. G., et al. (1999) Genome Res. 9: 1198–203.
42. Wallner, B. P., et al. (1986) Nature 320: 77–81.
43. Weterman, M. A., et al. (1995) Int. J. Cancer 60: 73–81.
44. Wittwer, C. T., et al. (1997) Biotechniques 22: 130–1, 134–8.
45. Wu, J. T. (1999) Ann. Clin. Lab. Sci. 29: 106–11.
46. Zeng, H., et al. (1999) Cancer Res. 59: 5964–7.

We claim:

1. A method of specifically delivering a reagent to a glioblastoma, comprising the step of:

contacting cells of the glioblastoma with an antibody which is conjugated to a reagent, wherein the antibody specifically binds to an extracellular epitope of glycoprotein (transmembrane) nmb (GPNMB) (SEQ ID NO:17), whereby the reagent is delivered to the cell.

2. The method of claim 1 wherein the glioblastoma is multidrug-sensitive.

3. The method of claim 1 wherein the reagent is a chemotherapeutic agent.

4. The method of claim 1 wherein the reagent is a cytotoxin.

5. The method of claim 1 wherein the reagent is a non-radioactive label.

6. The method of claim 1 wherein the reagent is a radioactive compound.

7. The method of claim 1 wherein the glioblastoma is in a human.

* * * * *